United States Patent [19]

Patel

[11] Patent Number: 5,000,743
[45] Date of Patent: Mar. 19, 1991

[54] CATHETER ASSEMBLY AND METHOD OF PERFORMING PERCUTANEOUS TRANSLUMINAL CORONARY ANGIOPLASTY

[76] Inventor: Piyush V. Patel, 3401 Salisbery, Midland, Tex. 79703

[21] Appl. No.: 284,843

[22] Filed: Dec. 13, 1988

Related U.S. Application Data

[63] Continuation of Ser. No. 19,688, Feb. 27, 1987, Pat. No. 4,832,028.

[51] Int. Cl.$^5$ .............................................. A61M 29/00
[52] U.S. Cl. ..................................... 606/194; 604/96; 604/101
[58] Field of Search ................... 128/344; 604/96, 101, 604/102; 606/191–196, 164, 165

[56] References Cited

U.S. PATENT DOCUMENTS

| | | |
|---|---|---|
| 3,430,631 | 3/1969 | Abramson . |
| 3,833,003 | 9/1974 | Taricco . |
| 3,896,816 | 7/1975 | Mattler . |
| 3,902,492 | 9/1975 | Greenhalgh . |
| 4,117,836 | 10/1978 | Erickson . |
| 4,195,637 | 4/1980 | Gruntzig et al. . |
| 4,259,960 | 4/1981 | Taylor . |
| 4,265,848 | 5/1981 | Rüsch . |
| 4,290,428 | 9/1981 | Durand . |
| 4,299,226 | 11/1981 | Banka . |
| 4,323,071 | 4/1982 | Simpson et al. . |
| 4,351,341 | 9/1982 | Goldberg . |
| 4,423,725 | 1/1984 | Baran . |
| 4,445,892 | 5/1984 | Hussein et al. . |
| 4,453,545 | 6/1984 | Inoue . |
| 4,493,697 | 1/1985 | Krause et al. . |
| 4,531,936 | 7/1985 | Gordon . |
| 4,581,017 | 4/1986 | Sahota . |
| 4,601,706 | 7/1986 | Aillón . |
| 4,610,662 | 9/1986 | Weikl et al. . |
| 4,624,657 | 11/1986 | Gould et al. . |
| 4,655,746 | 4/1987 | Daniels et al. . |
| 4,689,041 | 8/1987 | Corday et al. . |
| 4,790,315 | 12/1988 | Mueller, Sr. et al. .............. 128/344 |

Primary Examiner—C. Fred Rosenbaum
Assistant Examiner—Kathleen Daley
Attorney, Agent, or Firm—Herbert J. Hammond

[57] ABSTRACT

A catheter assembly and a method of performing percutaneous transluminal coronary angioplasty. The catheter assembly has a dilating catheter and a guiding catheter. The guiding catheter has an inflatable balloon near the tip for engaging the inner surface of the coronary lumen when inflated. The guiding catheter also has a side hole for perfusion of blood through the guiding catheter while the balloon on the guiding catheter is inflated. The balloon on the guiding catheter can be repeatedly inflated and deflated, and radiopaque material may be used to inflate the balloon on the guiding catheter. The method of performing percutaneous transluminal coronary angioplasty includes inserting the tip of the guiding catheter into a coronary lumen of a coronary artery, and inflating the balloon on the tip of the guiding catheter until the balloon engages the inner surface of the coronary lumen. A dilating catheter is then passed within the guiding catheter through a stenotic lesion within the coronary lumen. The balloon on the tip of the guiding catheter is deflated, and a balloon on the dilating catheter is inflated to dilate the stenotic lesion. The balloon on the dilating catheter is then deflated and the catheter assembly is removed from the coronary lumen.

6 Claims, 1 Drawing Sheet

CATHETER ASSEMBLY AND METHOD OF PERFORMING PERCUTANEOUS TRANSLUMINAL CORONARY ANGIOPLASTY

This is a continuation of Application No. 07/019,688 filed on Feb. 27, 1987, now U.S. Pat. No. 4,832,020.

TECHNICAL FIELD

This invention relates in general to medical equipment and procedures. In particular, the invention relates to a catheter assembly and a method of using the catheter assembly to perform a medical procedure known as percutaneous transluminal coronary angioplasty.

BACKGROUND AND SUMMARY OF THE INVENTION

The purpose of percutaneous transluminal coronary angioplasty is to open a coronary artery which has become partially blocked by a stenotic lesion. A stenotic lesion is an abnormal narrowing of an artery due to injury or disease.

The procedure involves the introduction of a catheter system into the heart, by way of the femoral artery, under local anesthesia. The catheter system includes a guiding catheter and a dilating catheter. The end of the guiding catheter is inserted into the opening of the coronary artery.

The dilating catheter is passed through the guiding catheter into the coronary artery. The tip of the dilating catheter is passed through the stenotic lesion in the coronary artery. A balloon on the tip of the dilating catheter is then inflated with a fluid. The balloon forces the blockage open and enlarges the lumen, or passage, through the artery.

A problem sometimes develops with this technique, when the dilating catheter has to pass through a tight stenosis or blockage. The reactionary force on the catheter assembly may cause the guiding catheter to slip out of the coronary opening. This results in an unstable condition, and makes it much more difficult to pass the dilating catheter through the stenotic lesion.

The catheter assembly of the invention overcomes this problem by providing an inflatable balloon near the tip of the guiding catheter. After the guiding catheter has been inserted into the opening of the coronary artery, the balloon is inflated. The balloon engages the inner surface of the coronary artery, and stabilizes the guiding catheter. The dilating catheter is then passed through the guiding catheter and through the stenotic lesion, without forcing the guiding catheter out of the coronary lumen.

Side holes in the guiding catheter allow blood to bypass the inflated balloon on the guiding catheter. Otherwise, the inflated balloon would obstruct the flow of blood to the coronary artery.

DESCRIPTION OF THE PREFERRED EMBODIMENT

Figure 1:
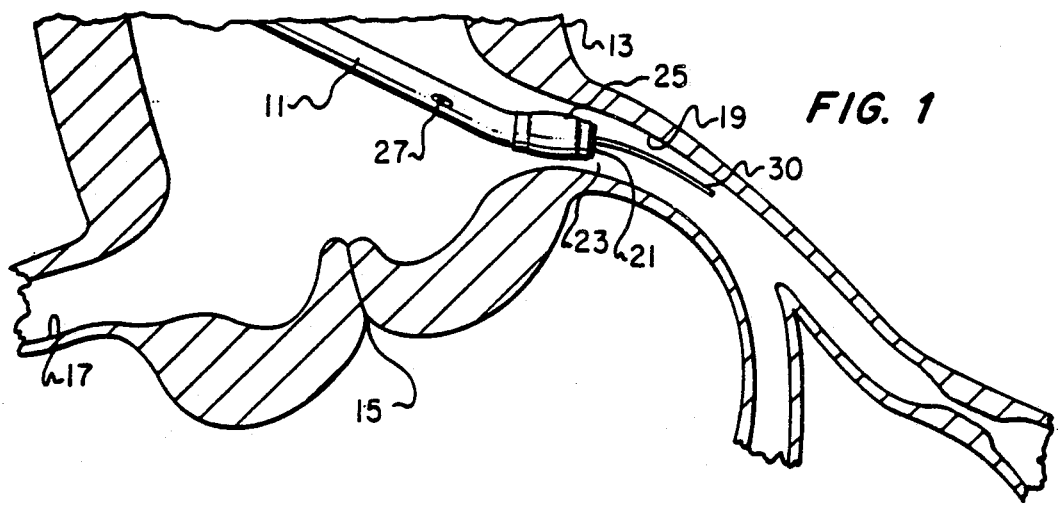
FIG. 1 is a side view of a guiding catheter of the invention, with the tip of the catheter inserted into a coronary lumen.

FIG. 1 shows the guiding catheter 11 of the invention. The guiding catheter 11 has been passed through the femoral artery to the aorta 13. FIG. 1 shows only a section of the aorta 13, the aortic valve 15, the right main coronary artery 17, and the left main coronary artery 19.

The tip 21 of the guiding catheter 11 is shown inserted into the opening, or ostium 23, of the left main coronary artery 19. Other guiding catheters may be shaped differently, for insertion elsewhere, such as into the right main coronary artery 17 or into the aortic valve 15. The left coronary guiding catheter 11, shown in FIG. 1, is shown merely as an example.

The guiding catheter 11 has an inflatable balloon 25 near the tip 21. In FIG. 1, the balloon 25 is deflated.

The guiding catheter 11 also has a side hole 27 above the balloon 25. The side hole 27 passes through the guiding catheter 11 to allow blood to flow from the aorta 13, through the side hole 27, and out the tip 21 of the guiding catheter 11.

Figure 2:
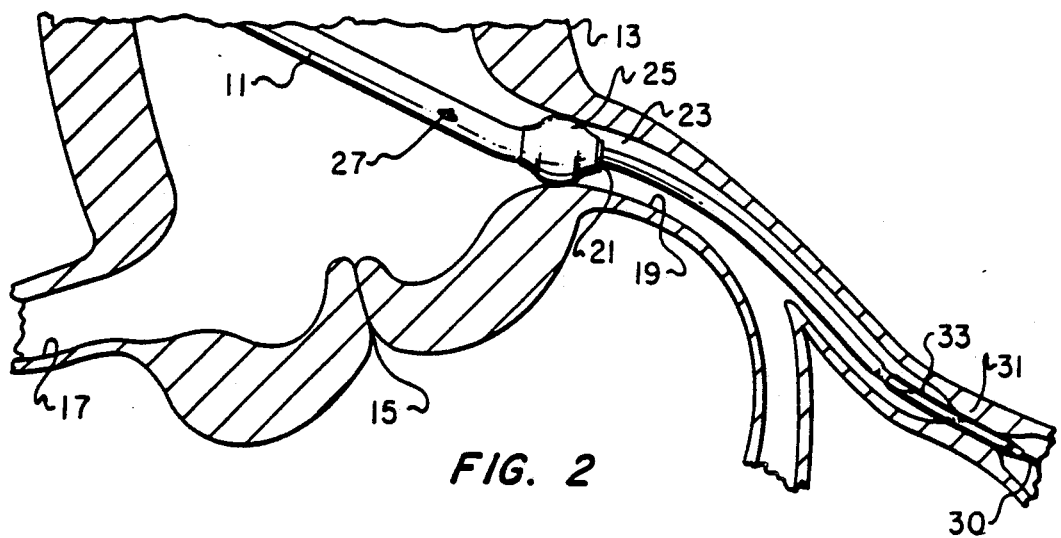
FIG. 2 is a side view of the catheter assembly of the invention.

In FIG. 2, the balloon 25 of the guiding catheter 11 is shown inflated. When the balloon 25 is inflated, the balloon 25 engages the inner surface of the coronary lumen of the left main coronary artery 19.

FIG. 2 also shows the dilating catheter 29, which extends through the guiding catheter 11 and out into the left main coronary artery 19. The dilating catheter 29 has been passed along a guide wire 30 through a stenotic lesion 31 on the inner surface of the left main coronary artery 19. An inflatable balloon 33 of the dilating catheter 29 has been positioned within the stenotic lesion 31.

Figure 3:
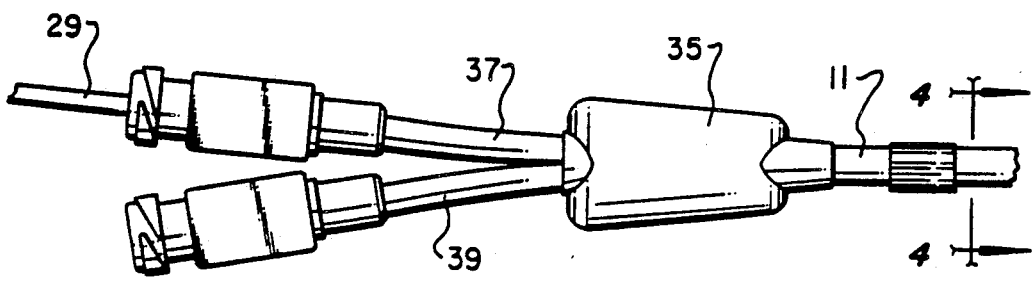
FIG. 3 is a side view of the proximal end of the guiding catheter of the invention.
Figure 4:
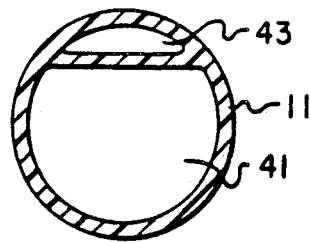
FIG. 4 is a sectional view of the guiding catheter, as seen along lines 4—4 in FIG. 3.

The proximal end of the guiding catheter 11 is illustrated in FIG. 3. An adapter body 35 is connected to the proximal end of the guiding catheter 11. The adapter body 35 is a Y-shaped body, which has two access conduits 37, 39. Access conduit 37 leads to the main lumen 41 of the guiding catheter 11, shown in FIG. 4. The main lumen 41 of the guiding catheter 11 is the conduit through which the dilating catheter 29 is passed.

The second access conduit 39 leads to a small side lumen 43 in the guiding catheter 11. Normal saline solution, or a mixture of water and radiopaque material, may be injected through the second access conduit 39 and the side lumen 43 to inflate the balloon 25 on the guiding catheter 11. The saline solution or radiopaque material may also be removed through the access conduit 39 to deflate the balloon 25 on the guiding catheter 11.

The catheter assembly of the invention is used in a method of performing percutaneous transluminal coronary angioplasty. The guiding catheter 11 is inserted through the femoral artery into the aorta 13. The tip 21 of the guiding catheter 11 is inserted into the ostium 23 of the left main coronary artery 19.

Saline solution or radiopaque material is then injected through the access conduit 39 to inflate the balloon 25 on the guiding catheter 11. The balloon 25 is inflated until it engages the inner surface of the coronary lumen 19. The engagement between the balloon 25 on the guiding catheter 11 and the ostium 23 of the main coronary artery 19 locks the guiding catheter 11 in place.

Blood is perfused through the side hole 27 and the tip 21 of the guiding catheter 11 into the main coronary artery 19. Blood flow is thus not restricted by the inflated balloon 25 on the guiding catheter 11.

The dilating catheter 29 is then passed through the guiding catheter 11 until the balloon 33 on the dilating catheter 29 passes through the stenotic lesion 31 in the coronary artery 19. Saline solution is then inserted through the lumen of the dilating catheter 29 to inflate the balloon 33 on the dilating catheter 29. The balloon 33 on the dilating catheter 29 dilates the lesion 31.

The saline solution is then removed from the dilating catheter 29 to deflate the balloon 33. The dilating catheter 29 is then removed from the area of the lesion 31. If the dilating catheter 29 needs to be repositioned, the balloon 25 on the guiding catheter 11 can be reinflated to hold the guiding catheter 11 in place.

The catheter assembly of the invention and the method of using the catheter assembly have an advantage over the assemblies and methods of the prior art. The balloon 25 on the guiding catheter 11 holds the tip 21 of the guiding catheter 11 in the ostium 23 of the coronary artery 19. This holds the guiding catheter 11 in place, allowing the dilating catheter 29 to be passed through tight stenotic lesions 31 more easily. Further, although the balloon 25 on the guiding catheter 11 contacts the inner surface of the coronary artery 19, blood flow is not restricted. Blood is perfused through the side hole 27 in the guiding catheter 11.

Only the preferred embodiment of the invention has been illustrated. It should be understood that the invention is not limited to the embodiment disclosed, but is capable of numerous rearrangements, modifications, and substitutions of parts and elements without departing from the spirit of the invention.

I claim:

1. A catheter assembly for performing percutaneous transluminal coronary angioplasty, said assembly comprising:

a dilating catheter having proximate and distal ends;

a dilating balloon, said dilating balloon being formed at the distal end of said dilating catheter;

means for inflating said dilating balloon;

a guide catheter having proximate and distal ends, said guide catheter defining a first lumen having a hollow open tip at the distal end thereof, a second lumen, and an aperture formed in the wall of said catheter adjacent the distal end of said catheter, said aperture communicating with said first lumen and said hollow tip to form a blood perfusion channel, said first lumen having a diameter sufficient to slidably receive said dilation catheter while simultaneously allowing blood to perfuse around said dilation catheter to an arterial area between said hollow tip and said dilation balloon;

a stabilizing balloon formed at the distal end of said guide catheter located between said aperture and said distal hollow tip, said stabilizing balloon being adapted to engage the walls of the coronary artery when inflated with sufficient force to stabilize said dilating catheter and dilating balloon when said dilating balloon is inflated, said second lumen communicating with said stabilizing balloon to provide means for inflating said stabilizing balloon.

2. The catheter assembly of claim 1 wherein a plurality of apertures communicate with said first lumen and hollow tip to form blood perfusion means.

3. The catheter assembly of claim 1 wherein said assembly further comprises a Y-shaped body, said body defining access channels to provide access to said second lumen and said dilating catheter.

4. The catheter assembly of claim 1 wherein said guide balloon and said dilating balloon may be repeatedly inflated and deflated.

5. The catheter assembly of claim 1 wherein fluid containing a radiopaque material is used to inflate said guide balloon.

6. The catheter assembly of claim 1 wherein fluid containing radiopaque material is used to inflate said dilating balloon.

* * * * *